(12) United States Patent
Agar et al.

(10) Patent No.: US 8,945,941 B2
(45) Date of Patent: Feb. 3, 2015

(54) TISSUE SAMPLE PREPARATION AND MALDI MS IMAGING THEREOF

(75) Inventors: Jeffrey N. Agar, Newton, MA (US); Nathalie Y. R. Agar, Newton, MA (US)

(73) Assignees: Brandeis University, Waltham, MA (US); The Brigham and Women's Hospital, Inc., Boston, MA (US)

( * ) Notice: Subject to any disclaimer, the term of this patent is extended or adjusted under 35 U.S.C. 154(b) by 1619 days.

(21) Appl. No.: 12/302,126

(22) PCT Filed: May 24, 2007

(86) PCT No.: PCT/US2007/012597
§ 371 (c)(1),
(2), (4) Date: Aug. 27, 2009

(87) PCT Pub. No.: WO2007/139989
PCT Pub. Date: Dec. 6, 2007

(65) Prior Publication Data
US 2009/0325222 A1    Dec. 31, 2009

Related U.S. Application Data

(60) Provisional application No. 60/808,755, filed on May 26, 2006.

(51) Int. Cl.
| | |
|---|---|
| G01N 1/00 | (2006.01) |
| G01N 1/36 | (2006.01) |
| G01N 1/31 | (2006.01) |
| G01N 31/00 | (2006.01) |
| H01J 49/26 | (2006.01) |
| H01J 27/24 | (2006.01) |
| G01N 1/30 | (2006.01) |

(52) U.S. Cl.
CPC . *G01N 1/312* (2013.01); *G01N 1/30* (2013.01)
USPC ........ 436/174; 250/281; 250/288; 250/423 P; 435/7.21; 435/174; 436/173

(58) Field of Classification Search
None
See application file for complete search history.

(56) References Cited

U.S. PATENT DOCUMENTS

| | | | | |
|---|---|---|---|---|
| 6,004,770 | A * | 12/1999 | Nelson | 435/23 |
| 6,071,610 | A | 6/2000 | Jarrell et al. | |
| 6,225,047 | B1 * | 5/2001 | Hutchens et al. | 435/5 |
| 6,391,649 | B1 * | 5/2002 | Chait et al. | 436/173 |
| 7,095,018 | B2 | 8/2006 | Barnes et al. | |
| 7,445,907 | B2 | 11/2008 | Everett et al. | |
| 2002/0171037 | A1 | 11/2002 | Ellson et al. | |
| 2004/0026615 | A1 | 2/2004 | Ellson et al. | |
| 2004/0137420 | A1 | 7/2004 | Yasuda et al. | |
| 2005/0112743 | A1 | 5/2005 | Potthoff et al. | |
| 2005/0244866 | A1 | 11/2005 | Boschetti et al. | |
| 2006/0078923 | A1 | 4/2006 | McKernan et al. | |

OTHER PUBLICATIONS

Bruker Daltonics "High Resolution Molecular Imaging of Small Molecules by MALDI-TOF" Bruker Daltonics Application Note # FTMS-37 <URL:www.bdal.com/uploads/media/FTMS-37_Nov. 08-eBook.pdf>, Jun. 2008, Abstract archived Feb. 15, 2004, 5 pages.*
Agar, NY, Yang, HW, Carroll, RS Black, PM, and Agar, JM "Matrix Solution Fixation: Histology-Compatible Tissue Preparation for MALDI Mass Spectrometry Imaging" Anal. Chem., 2007, 79(19), pp. 7416-7423.*
Chaurand, P, Schwartz,SA, Billheimer, D, Xu, BJ, Crecelius, A, Caprioli, RM "Integrating Histology and Imaging Mass Spectrometry" Anal. Chem., 2004 (published online Jan. 9, 2004), 76(4), 1145-1155.*
Lemaire,R; Wisztorski, M; Desmons,A;Tabet, JC; Day, R; Salzet, M; and Fournier, I "MALDI-MS Direct Tissue Analysis of Proteins: Improving Signal Sensitivity Using Organic Treatments" Anal. Chem. Oct. 15, 2006, 78 (20), pp. 7145-7153.*
Agar, N Y R; Yang H W; Carroll, R S; Black, P W; Agar, J N, "Matrix Solution Fixation: Histology-Compatible Tissue Preparation for MALDI Mass Spectrometry Imaging" Anal. Chem. Oct. 1, 2007, 79(19), pp. 7416-7423.*
Lemaire,R; Wisztorski, M; Desmons,A;Tabet, JC; Day, R; Salzet, M; and Fournier, I "MALDI-MS Direct Tissue Analysis of Proteins: Improving Signal Sensitivity Using Organic Treatments" Anal. Chem. Oct. 15, 2006 (epub Sep. 15, 2006), 78 (20), pp. 7145-7153 (DOI: 10.1021/ac060565z).*
Agar, N Y R; Yang H W; Carroll, R S; Black, P W; Agar, J N, "Matrix Solution Fixation: Histology-Compatible Tissue Preparation for MALDI Mass Spectrometry Imaging" Anal. Chem. Oct. 1, 2007 (epub Sep. 7, 2007), 79(19), pp. 7416-7423 (DOI: 10.1021/ac071460e).*
International Search Report for PCT/US2007/12597 mailed Feb. 13, 2008, 3 pages.
Caldwell, R.L. et al., "Tissue Profiling by Mass Spectrometry," *Molecular and Cellular Proteomics* 4: 394-401 (2005).
Sugiura, Y. et al., "Thin Sectioning Improves the Peak Intensity and Signal-to-Noise Ratio in Direct Tissue Mass Spectrometry," *J. Mass Spectrom. Soc. Jpn.* 54(2): 45-48 (2006).

* cited by examiner

*Primary Examiner* — Jon P Weber
*Assistant Examiner* — Aaron J Kosar
(74) *Attorney, Agent, or Firm* — Foley Hoag LLP (57) ABSTRACT

Aspects of the present invention relate to a method for the preparation of samples for MALDI MS imaging. Certain embodiments relate to a method of matrix deposition for samples, wherein tissue sections are prepared via a synergistic combination of fixation with matrix. In certain embodiments, tissue is fixed with cold solvent, according to well-established histology protocols, and in the presence of matrix, allowing for high resolution spatial mapping of protein, lipid, sugar, and/or nucleic acid distribution. In certain embodiments, the present invention relates to fixation with matrix of whole organisms. In certain embodiments, animals are perfused with fixation and matrix mixtures, which allows for direct mass spectrometry analysis.

11 Claims, 7 Drawing Sheets

(56) References Cited

OTHER PUBLICATIONS

TISSUE SAMPLE PREPARATION AND MALDI MS IMAGING THEREOF

RELATED APPLICATIONS

This application claims the benefit of priority to Patent Cooperation Treaty Application number PCT/US2007/012597, filed May 24, 2007; which claims the benefit of priority to the filing date of U.S. Provisional Patent Application Ser. No. 60/808,755, filed May 26, 2006; the entirety of which are hereby incorporated by reference.

BACKGROUND OF THE INVENTION

Disease diagnosis and therefore treatment rely upon observations of tissue and cellular characteristics, such as proliferation, cellular and nuclear morphology, vascularization, and specific biomarkers. For example, both the choice of treatment and the risks taken during surgical resection of a tumor mass in the brain are dictated by tumor type and malignancy grade. Tangentially, detailed pathology characterization is revealing considerable overlap in the molecules involved in one disease and the next, consistent with disease continuum rather than discrete disease states. For instance, the lines between Alzheimer's, Pick's, and Parkinson's diseases are often blurred (Galpern and Lang (2006) *Ann Neurol* 59:449), as are the lines between gradations of a given tumor type (see Caprioli (2005) *Cancer Res* 65:10642; Schwartz et al. (2005) *Cancer Res* 65:7674; Iwadate et al. (2004) *Cancer Res* 64:2496). As the list of overlapping molecules involved in cancers and other diseases grows, so does the need for comprehensive molecular profiling as part of diagnosis (Schwartz, ibid; Schwartz et al. (2004) *Clin Cancer Res* 10:981). The recent adaptation of mass spectrometers and their respective computer applications to accommodate tissue analysis (Stoeckli et al. (2001) *Nat Med* 7:493) provides such a comprehensive molecular profile (Schwartz, ibid; Iwadate, ibid; Rahman et al. (2005) *Am J Respir Crit Care Med* 172:1556; Yanagisawa et al. (2003) *Lancet* 362:433; Chaurand et al. (2006) *Curr Opin Biotechnol* 17:431) and saves time compared to histology.

Mass spectrometry (MS) is a well-established technique used to characterize analytes by determining their molecular weight. Ordinarily, mass spectrometry involves the steps of: coating a sample presentation apparatus with an analyte, introducing the sample presentation apparatus into the mass spectrometer, volatilizing and ionizing the molecules of the analyte, accelerating the ionized analyte toward a detector by exposing the ions to an electric and/or a magnetic field, and analyzing the data to determine the mass-to-charge ratio of specific analyte ions. If an analyte remains intact throughout this process, data will be obtained that correspond to a molecular weight for the entire intact analyte ion. Typically however, it is also desirable to obtain data corresponding to the molecular weight of various fragments of the analyte.

Matrix-Assisted Laser Desorption Ionization (MALDI) is an ionization technique often used for mass spectrometric analysis of large and/or labile biomolecules, such as nucleotidic and peptidic oligomers, polymers, and dendrimers, as well as for analysis of nonbiomolecular compounds, such as fullerenes (Karas et al. (1987) *Int. J. Mass. Spectrom. Ion Processes* 78:53; Spengler and Kaufmann, (1992) *Analusis* 20:91). MALDI is considered a "soft" ionizing technique, in which both positive and negative ions are produced. The technique usually involves depositing a small volume of sample fluid containing an analyte on a substrate comprised of a photon-absorbing "matrix" material selected to enhance desorption performance. See Karas et al. (1988), "Laser Desorption Ionization of Proteins with Molecular Masses Exceeding 10,000 Daltons," *Anal. Chem.*, 60:2299-2301. Said matrix material is usually a crystalline organic acid that absorbs electromagnetic radiation near the wavelength of the laser. When co-crystallized with analyte, the matrix material assists in the ionization and desorption of analyte moieties. The sample fluid typically contains a solvent and the analyte. Once the solvent has been evaporated from the substrate, the analyte remains on the substrate at the location where the sample fluid has been deposited. Photons from a laser strike the substrate at the location of the analyte and, as a result, ions and neutral molecules are desorbed from the substrate. Prior to the development of MALDI, analysis of biomolecules by mass spectrometry was quite difficult, if not impossible, since no techniques were available that were gentle enough to volatize intact biomolecules without any degradation or fragmentation. MALDI techniques are particularly useful in providing a means for efficiently analyzing a large number of samples. In addition, MALDI is especially useful in the analysis of minute amounts of sample that are provided over a small area of a substrate surface.

Direct mass spectrometry analysis of a tissue sample affords a wealth of chemical information, providing a molecular landscape of a tissue. Unlike current immunohistochemistry methods, which analyze the concentration and distribution of only a single molecule per experiment, MS imaging provides information on hundred of molecules, affording a better correlation between molecular composition and disease pathology, and therefore a more accurate diagnosis. Indeed, the ability to image a sample with the objective to obtain the detailed spatial arrangement of compounds in an ordered target sample such as a slice of tissue using MALDI MS would be of enormous value in biological research. For example, selected ion surface maps of such samples could provide details of compound compartmentalization, site-specific metabolic processing, and selective binding domains for a very wide variety of natural and synthetic compounds.

Recently, mass spectrometry techniques involving laser desorption have been adapted for cellular analysis. For example, U.S. Pat. No. 5,808,300 to Caprioli describes a method for imaging biological samples with MALDI mass spectrometry. This method allows users to measure the distribution of a specific element or small molecule within biological specimens such as tissue slices or individual cells. In particular, the method can be used for the specific analysis of peptides in whole cells, e.g., by obtaining signals for peptides and proteins directly from tissues and blots of tissues. In addition, the method has been used to desorb relatively large proteins from tissues and blots of tissues in the molecular weight range beyond about 80 kiloDaltons. From such samples, hundreds of peptide and protein peaks can be recorded in the mass spectrum produced from a single laser-ablated site on the sample. When a laser ablates the surface of the sample at multiple sites and the mass spectrum from each site is saved separately, a data array is produced, which contains the relative intensity of any given mass at each site. In the MALDI MS imaging experiment (MSI), hundreds of closely spaced MALDI MS spectra are taken in a grid pattern where each spectrum is analogous to a pixel (Gusev et al. (1995) *Anal. Chem.* 67:4565; Stoeckli et al. (1999) *J Am Soc Mass Spectrom* 10:67; Caprioli et al. *Anal. Chem.* (1997) 69:4751). Each pixel contains information on the mass and intensity of hundreds of biomolecules, which can be translated into a spatial map of molecular distribution and abundance. An image of the sample surface can then be constructed for any given molecular weight, effectively representing a compositional map of the sample surface.

Accordingly, in order to perform mass spectrometry imaging, molecules must be transferred from the tissue and into the gas phase. As described above, this transfer requires a laser within the mass spectrometer, and a matrix which is applied to the tissue section. The matrix is a small acid that crystallizes on the sample, and upon absorbing laser energy is vaporized along with molecules from the tissue. For efficient desorption of large molecules (10 kDa and greater) by MALDI, sinapinic acid is a commonly used matrix. The matrix solution most often applied to tissue samples is 20-30 mg sinapinic acid/ml and about 0.1% trifluoroacetic acid (TFA), in a solvent mixture of 50:50 volume ratio of acetonitrile to water. Hence, all current methods of matrix deposition on tissue slices, such as the solution base described, considerably perturb tissue integrity, resulting in the solubilization and extraction of proteins and peptides from the tissue and their subsequent diffusion from biological location (Gusev, ibid.). Delocalization of proteins has a deleterious effect on image quality. Spatial resolution is lost, and the MS image becomes "blurred." To minimize protein diffusion in the tissue section, practitioners commonly use a method referred to as "spotting." The goal of spotting is to apply very small droplets of solution, and since proteins can only diffuse within the drop, the "blurring" is limited to smaller area. Spotting involves either manual deposition using a pipette, or using a recently patented acoustic reagent multispotter device (Aerni et al. (2006) *Anal. Chem.* 78(3):827-34; U.S. Pat. Nos. 6,707,038, 6,809,319, and 6,855,925 all to Ellson et al.). The diameter of the spots is on average 1 mm, at least one thousand times too large for many histology-based diagnoses. Indeed, there are considerable drawbacks to this practice. Current methods of sample preparation associated with this approach: (1) are expensive (the device of Caprioli, Ellson, et al. costs approximately $300,000, requiring significant capital investment); (2) are time consuming (hours vs. minutes to prepare and deposit sample); (3) do not provide images of sufficient resolution (from 0.2 mm for the acoustic reagent multispotter to 1 millimeter resolution for manual deposition currently, whereas 1 micrometer is needed); (4) do not provide a contiguous image or profile of the tissue; and (5) manual spotting is not reproducible.

Another approach used to cover tissue samples with matrix solution without causing considerable protein displacement is referred to as "spraying." This method consists of applying the matrix solution uniformly on the tissue section using consecutively minimal volumes of solution to minimize the time that the tissue is in the presence of the solvent. The spraying of matrix solution is typically achieved using a nebulizer, paintbrush or modified electrospray source. Although some practitioners precede spraying or spotting by ethanol fixation, the acetonitrile/water based solution of matrix can still dissolve and displace fixed proteins. Following our own attempts to improve spraying using a modified electrospray source (Schwartz et al. (2003) *J Mass Spectrom* 38:699), we concluded that this method is still not suited for use in a clinical setting. Although good images can be produced, image quality was inconsistent and spatial resolution was operator-dependent.

Notwithstanding its promise, MS imaging has not yet been incorporated as a medical diagnostic, in part due to a lack of facile, reproducible means of tissue preparation. A sample preparation method of matrix deposition for tissue sections is needed for MALDI MS analysis, which preserves the spatial location of proteins during processing. An objective of the present invention and all attendant embodiments for MALDI MS imaging and sample preparation related thereto is to provide medicine with safe diagnostic strategies that are readily accessible to any established pathology or research laboratory.

SUMMARY OF THE INVENTION

Aspects of the present invention relate to a method for the preparation of samples for MALDI MS imaging. Certain embodiments relate to a method of matrix deposition for samples, wherein tissue sections are prepared via a synergistic combination of fixation with matrix. In certain embodiments, tissue is fixed with cold solvent, according to well-established histology protocols, and in the presence of matrix, allowing for high resolution spatial mapping of protein, lipid, sugar, and/or nucleic acid distribution. In certain embodiments, the present invention relates to fixation with matrix of whole organisms. In certain embodiments, animals are perfused with fixation and matrix mixtures, which allows for direct mass spectrometry analysis.

Aspects of the present invention provide the first such inexpensive, expeditious, and reproducible methodologies for sample preparation that are compatible with histology protocols currently employed by pathologists for diagnosing diseases. Techniques provided by the present invention are broadly applicable toward the preparation of any sample for MS imaging upon synergistic utilization of fixation and matrix and improve the quality of spectra and provide images that do not have a perforated appearance, which marks an improvement over current practices. In certain embodiments, subcellular spatial resolution is achieved. The high-quality preparation and execution of methods of the present invention have the potential to improve diagnosis of malignancies involving a variety of biopsy types.

BRIEF DESCRIPTION OF THE FIGURES

FIG. 3 depicts the immunohistochemistry of mouse brain tissue. Images are representations of optical stacks from the whole tissue thickness, unless otherwise specified. Cell nuclei are depicted using DAPI staining and different proteins are depicted through labeling with an FITC or Alexa 488 secondary antibody probe, and visualized by confocal microscopy with a 63× oil objective; scale bars as indicated: (a-d) Comparison of the effect of different fixations on nuclei and neurofilaments integrity between standard paraformaldehyde (a), cold methonal:ethanol:acetonitrile:about 0.1% TFA (b), cold acetone (c), and after sinapinic acid solution fixation followed by matrix removal using methanol (d); (e-h) Distribution patters of a newly characterized soluble protein with distinctive tissue distribution, and perinuclear subcellular localization. Tissue slices were prepared using cold acetone (e, f; 1-2 µm optical slices), standard paraformaldehyde fixation (g), and new cold methanol:ethanol:acentonitrile:about 0.1% TFA solution in accordance with the present invention (h). Panels i and j compare the distribution of MAP2 in mouse brain tissue fixed with paraformaldehyde (i) and with new matrix fixation solution at −20° C. (j).

FIG. 5 depicts (a,b) H&E staining of a pair of progressive meningioma samples, grade II and III respectively, representing common histology-based tumor diagnosis. Light microscopy with 40× objective. The samples present heterogeneity that is observed in higher degree of malignancy, and the arrows are showing mitotic events. Samples were fixed with paraformaldehyde, paraffin embedded, and diagnosed by a pathologist; (c,e,g) and (d,f,h) display MALDI MS molecular ion images of selected masses from a distinct pair of progressive meningioma samples, grade II and III respectively. Scale bars=1 mm. The distribution of the ions presented also indicates heterogeneity, with a specific molecular signature. Specimens were prepared by sinapinic acid solution fixation (ethanol:methanol:acetonitrile:about 0.1% TFA) at −20° C. for 5 minutes.

DETAILED DESCRIPTION OF THE INVENTION

Aspects of the present invention relate to a method for the preparation of samples for analysis by MALDI MS imaging. This sample preparation method is compatible with the histology protocols currently employed by pathologists for diagnosing diseases.

Certain embodiments provide a protocol for matrix deposition of samples, e.g., tissue sections, which combines histology knowledge and mass spectrometry analysis requirements, referred to herein as a "matrix solution fixation" method, wherein fixation of said sample and deposition of the matrix are combined in a single step. This method prevents proteins from moving or diffusing from their original location; it has been successfully applied in major ways, and is being developed further to suit particular application requirements. In certain embodiments, the present invention relates to fixing tissue with cold solvent, according to well-established histology protocols, and in the presence of matrix. Said established immunohistochemistry fixation protocols exploit specific chemical action such as protein denaturation at low pH, protein precipitation induced by solvents, and temperature controlled protein diffusion. Aspects of the present invention also address the distinction between protein precipitation and agglomeration by providing for the optional selection of an appropriate solvent/temperature combination, as agglomeration is more easily reversible upon temperature increase.

In certain embodiments of the present invention, frozen tissue sections (e.g., brain and/or spinal cord) may be prepared and tested according to the following solvent/matrix solutions: (a) acetone and 30 mg/mL of either sinapinic acid or α-cyano-4-hydroxycinnamic acid (HCCA) at −20° C.; (b) methanol and 30 mg/mL of either sinapinic acid or HCCA at −20° C.; (c) about 95% ethanol: about 5% acetic acid combination and 25 mg/mL of either sinapinic acid or HCCA at 4° C.; (d) about 50% methanol:about 50% acetone combination and 30 mg/mL of either sinapinic acid or HCCA at −20° C.; (e) about 10% glacial acetic acid:about 30% chloroform: about 60% absolute ethanol combination and 30 mg/mL of either sinapinic acid or HCCA; (f) about 50% methanol:about 50% ethanol combination and 30 mg/mL of either sinapinic acid or HCCA at −20° C.; (g) 1 part methanol:1 part ethanol:1 part (about 50% acetonitrile: about 50% aqueous solution of about 0.1% trifluoroacetic acid) combination and 30 mg/mL of either sinapinic acid or HCCA at −20° C. and/or 4° C. In each case, the preceding histopathology fixation solutions can be combined with matrix to provide MS imaging-ready samples. Optimum matrix crystal production and distribution and quality of mass spectrometry data were observed using about 95% ethanol:about 5% acetic acid combination and 25 mg/mL of either sinapinic acid or HCCA at 4° C.

In certain embodiments, the present invention relates to a matrix solution fixation method for whole organisms. In animal studies, intact mice have been perfused with different "matrix solution fixation" mixtures, e.g., (a) Carnoy's fixative (10 mL glacial acetic acid:30 mL chloroform:60 mL absolute ethanol), and (b) about 95% ethanol: about 5% acetic acid combination and 25 mg/mL sinapinic acid at 4° C. Perfusion of animals with fixative prior to mass spectrometry analysis deprives the tissue of blood, and provides fixed tissue suitable for direct mass spectrometry analysis. When animals are perfused with a Carnoy's/matrix solution, one is able to detect the presence of the matrix within the brain periphery by mass spectrometry. This demonstration of tissue fixation and matrix incorporations using whole animal perfusion is remarkable.

Exemplary fixatives, commonly used in histology (i.e., histopathology, histochemistry, immunohistochemistry), include, but are not limited to: aldehydes (e.g., formaldehyde (paraformaldehyde, formalin), glutaraldehyde, acrolein (acrylic aldehyde), glyoxal (ethanedial, diformyl), malonaldehyde (malonic dialdehyde), diacetyl (2,3-butanedione), and polyaldehydes; alcohols (i.e., protein-denaturing agents; e.g., acetic acid, methanol, ethanol); heavy metal oxidizing agents (i.e., metallic ions and complexes; e.g., osmium tetroxide, chromic acid); agents of unknown mechanism, such as chloro-s-triazides, cyanuric chloride, carbodiimides, diisocyanates, diimido esters, diethylpyrocarbonate (diethyl oxydiformate, ethoxyformic anhydrate), picric acid, mercuric chloride (corrosive sublimate, bichloride of mercury), and other salts of mercury, and acetone. What is more common is to employ such agents in combination. Such combinations give rise to commonly termed formulations known to those in the art, such as Carnoy's fixatives, methacran, Wolman's solution, Rossman's fluid, Gendre's fluid, Bouin's fluid, Zenker's fluid, Helly's fluid, B5 fixative, Susa fluid, Elftman's fixative, Swank and Davenport's fixative, Lillie's alcoholic lead nitrate, and cetylpyridinium chloride (C.P.C.). Additives can include, but are not limited to, such entities as tannic acid, phenol, transition metal salts (zinc), lanthanum, lithium, potassium.

MALDI MS matrix may be any material that absorbs light energy at a frequency easily accessible by a laser. It is further useful that said matrix materials gain physical access to biomolecules and are unreactive with respect to biomolecules. Example matrices include, but are not limited to: nicotinic acid, pyrozinoic acid, vanillic acid, succinic acid, caffeic acid, glycerol, urea or tris buffer (pH 7.3) and/or combinations thereof. More commonly employed matrices include α-cyano-4-hydroxycinnamic acid (HCCA), ferulic acid, 2,5-dihydroxybenzoic acid, sinapinic (or sinapic) acid, 3,5-dimethoxy, 4-hydroxy-trans-cinnamic acid, other cinnamic acid derivatives, gentisic acid, and/or combinations thereof.

Aspects of the present invention also relate to a method for sample preparation using matrix-coated sample carriers, wherein a sample carrier (e.g., a metal MALDI target, MALDI support, glass slide, ITO-coated glass slide, glass cover slip) is coated with matrix (i.e., deposited), and sample tissue is the mounted upon said matrix-coated carrier and subsequently fixed with solvents (i.e., using the solutions and methods of the present invention, or any solvent or solvent mixture that will dissolve the deposited MALDI matrix). In certain embodiments, such a method involves the following steps: (1) coating any MALDI sample carrier with matrix; (2) applying sample tissue to said matrix-coated sample support; and (3) applying a solution that will fix the tissue (including but not limited to low temperature). In certain embodiments, it may be observed that deposition of the matrix material is easier and gives rise to better data and protects the instrument. Sample carriers deposited with matrix material also facilitate the applications of methods of the present invention and the practical application of embodiments of the present invention, including the packaging of such materials in a diagnostic kit.

Selected Embodiments of the Invention

In certain embodiments, the present invention relates to a method for preparing a sample for analysis by mass spectrometry, comprising treating, at a temperature, said sample with a solution comprising a fixative and an analysis-enhancing material.

In certain embodiments, the present invention relates to the aforementioned method, wherein said analysis-enhancing material is first deposited onto a sample carrier to give a coated sample carrier.

In certain embodiments, the present invention relates to the above-mentioned method, further comprising mounting said sample upon said coated sample carrier prior to treating with said fixative.

In certain embodiments, the present invention relates to the either of the above-mentioned methods, wherein said sample carrier is selected from the group consisting of: metal targets, glass slides, or glass cover slips.

In certain embodiments, the present invention relates to the above-mentioned method, wherein said sample carrier is a metal target; and said metal target is polished stainless steel or ground stainless steel.

In certain embodiments, the present invention relates to the above-mentioned method, wherein said sample carrier is a glass slide or glass cover slip; and said glass slide or glass cover slip is coated with indium tin oxide (ITO).

In certain embodiments, the present invention relates to the aforementioned method, further comprising combining a fixative and an analysis-enhancing material to give a solution.

In certain embodiments, the present invention relates to the aforementioned method, further comprising incubating said sample for a period of time, at a temperature, and drying said incubated sample.

In certain embodiments, the present invention relates to the aforementioned method, wherein the period of time is about 10 minutes.

In certain embodiments, the present invention relates to the aforementioned method, wherein the temperature is about −20° C.

In certain embodiments, the present invention relates to the aforementioned method, wherein the period of time is about 10 minutes and the temperature is about −20° C.

In certain embodiments, the present invention relates to the aforementioned method, further comprising rinsing said incubated sample, and drying said rinsed incubated sample, and optionally rinsing said rinsed and dried incubated sample a second time, and drying said optionally rinsed sample.

In certain embodiments, the present invention relates to the aforementioned method, wherein the rinsing is done with a about 0.1% aqueous solution of trifluoroacetic acid (TFA).

In certain embodiments, the present invention relates to the aforementioned method, wherein said first rinse lasts a few seconds, and said second rinse lasts for about one minute.

In certain embodiments, the present invention relates to the aforementioned method, wherein the amount of about 0.1% aqueous solution of TFA used is about 10-20 µL for each rinse.

In certain embodiments, the present invention relates to the aforementioned method, further comprising freezing said sample.

In certain embodiments, the present invention relates to the aforementioned method, wherein said fixative is a histology fixation solution.

In certain embodiments, the present invention relates to the aforementioned method, wherein said fixative is selected from the group consisting of: (a) acetone; (b) methanol; (c) about 95% ethanol:about 5% acetic acid combination; (d) about 50% methanol:about 50% acetone combination; (e) about 10% glacial acetic acid:about 30% chloroform:about 60% absolute ethanol combination; (f) about 50% methanol: about 50% ethanol combination; and (g) 1 part methanol:1 part ethanol:1 part (about 50% acetonitrile:about 50% aqueous solution of about 0.1% TFA) combination.

In certain embodiments, the present invention relates to the aforementioned method, wherein said fixative is about 95% ethanol:about 5% acetic acid combination.

In certain embodiments, the present invention relates to the aforementioned method, wherein the temperature ranges from about −100° C. to about 100° C.

In certain embodiments, the present invention relates to the aforementioned method, wherein the temperature ranges from about −78° C. to about 37° C.

In certain embodiments, the present invention relates to the aforementioned method, wherein the temperature is about −20° C., about 4° C., about 37° C., or room temperature.

In certain embodiments, the present invention relates to the aforementioned method, wherein the temperature is about −20° C.

In certain embodiments, the present invention relates to the aforementioned method, wherein the temperature is about 4° C.

In certain embodiments, the present invention relates to the aforementioned method, wherein the temperature is about 37° C.

In certain embodiments, the present invention relates to the aforementioned method, wherein the temperature is room temperature.

In certain embodiments, the present invention relates to the aforementioned method, wherein said analysis-enhancing material is a mass spectrometry matrix material.

In certain embodiments, the present invention relates to the aforementioned method, wherein said mass spectrometry matrix material is a photo absorbing matrix material.

In certain embodiments, the present invention relates to the aforementioned method, wherein said mass spectrometry matrix material is selected from the group consisting of: nicotinic acid; pyrozinoic acid; vanillic acid; succinic acid; caffeic acid; glycerol; urea buffer (pH about 7.3); tris buffer (pH about 7.3); α-cyano-4-hydroxycinnamic acid (HCCA); ferulic acid; 2,5-dihydroxybenzoic acid; sinapinic acid; 3,5-dimethoxy-4-hydroxy-trans-cinnamic acid; cinnamic acid derivatives; gentisic acid; and combinations thereof.

In certain embodiments, the present invention relates to the aforementioned method, wherein the analysis-enhancing material is sinapinic acid or HCCA.

In certain embodiments, the present invention relates to the aforementioned method, wherein the analysis-enhancing material is sinapinic acid.

In certain embodiments, the present invention relates to the aforementioned method, wherein the analysis-enhancing material is HCCA.

In certain embodiments, the present invention relates to the aforementioned method, wherein the analysis-enhancing material is at a concentration of about 20-30 mg/mL.

In certain embodiments, the present invention relates to the aforementioned method, wherein the analysis-enhancing material is sinapinic acid at a concentration of about 20-30 mg/mL.

In certain embodiments, the present invention relates to the aforementioned method, wherein the analysis-enhancing material is HCCA at a concentration of about 20-30 mg/mL.

In certain embodiments, the present invention relates to the aforementioned method, wherein the analysis-enhancing material comprises a detectable label moiety.

In certain embodiments, the present invention relates to the aforementioned method, wherein said label moiety is fluorescent, radioactive, magnetic, biomolecular, or a combination thereof.

In certain embodiments, the present invention relates to the aforementioned method, wherein the sample is a whole organism.

In certain embodiments, the present invention relates to the aforementioned method, wherein the whole organism is an animal.

In certain embodiments, the present invention relates to the aforementioned method, wherein the animal is a mouse.

In certain embodiments, the present invention relates to the aforementioned method, wherein the sample is a cellular sample.

In certain embodiments, the present invention relates to the aforementioned method, wherein the sample is selected from the group consisting of a tissue sample, a cell culture, a single cell, cellular extract, or a plurality of cells immobilized on a substrate surface.

In certain embodiments, the present invention relates to the aforementioned method, wherein said tissue sample is animal tissue.

In certain embodiments, the present invention relates to the aforementioned method, wherein said animal tissue is mammalian tissue.

In certain embodiments, the present invention relates to the aforementioned method, wherein said mammalian tissue is primate, bovine, ovine, equine, porcine, rodent, feline, or canine.

In certain embodiments, the present invention relates to the aforementioned method, wherein the tissue is human.

In certain embodiments, the present invention relates to the aforementioned method, further comprising thaw-mounting said sample.

In certain embodiments, the present invention relates to the aforementioned method, wherein the thickness of the sample is less than or equal to about 16 μm.

In certain embodiments, the present invention relates to the aforementioned method, wherein: the fixative is selected from the group consisting of: (a) acetone; (b) methanol; (c) about 95% ethanol:about 5% acetic acid combination; (d) about 50% methanol:about 50% acetone combination; (e) about 10% glacial acetic acid:about 30% chloroform:about 60% absolute ethanol combination; (i) about 50% methanol: about 50% ethanol combination; and (g) 1 part methanol:1 part ethanol:1 part (about 50% acetonitrile about 50% aqueous solution of about 0.1% TFA) combination; and the analysis-enhancing material is mass spectrometry matrix material selected from the group consisting of: nicotinic acid; pyrozinoic acid; vanillic acid; succinic acid; caffeic acid; glycerol; urea buffer (pH about 7.3); tris buffer (pH about 7.3); α-cyano-4-hydroxycinnamic acid; ferulic acid; 2,5-dihydroxybenzoic acid; sinapinic acid; 3,5-dimethoxy, 4-hydroxy-trans-cinnamic acid; cinnamic acid derivatives; gentisic acid; and combinations thereof.

In certain embodiments, the present invention relates to the aforementioned method, wherein said fixative is about 95% ethanol:about 5% acetic acid combination, the analysis-enhancing material is sinapinic acid or HCCA, and the temperature is about 4° C.

In certain embodiments, the present invention relates to the aforementioned method, wherein said fixative is about 95% ethanol:about 5% acetic acid combination, the analysis-enhancing material is sinapinic acid, and the temperature is about 4° C.

In certain embodiments, the present invention relates to the aforementioned method, wherein said fixative is about 95% ethanol:about 5% acetic acid combination, the analysis-enhancing material is HCCA, and the temperature is about 4° C.

In certain embodiments, the present invention relates to a method of medical diagnosis comprising analyzing by mass spectrometry a sample prepared according to any one of the methods described above.

In certain embodiments, the present invention relates to the aforementioned method, wherein the analysis is conducted by MALDI mass spectrometry.

In certain embodiments, the present invention relates to the aforementioned method, wherein the analysis is conducted by MALDI MS imaging.

Aspects of the present invention are designed to prohibit proteins from diffusing during the process of MALDI matrix deposition, thereby maintaining their original location in sample tissue. As a measure of success, said tissue would maintain a heterogeneous distribution of proteins, whereas current methods lead to homogeneity as previously described.

In certain embodiments, the present invention relates to the following generalized methods and materials:

Tissue Slicing—In certain embodiments, sample tissues (e.g., mouse brains and/or spinal cords) are sectioned at 16 μm thickness, thaw-mounted on coverslips, and stored on dry ice until fixation. Said sections are routinely processed from frozen tissue, yet may be harvested from tissue in any state.

Preparation of Matrix Fixation Solution—In certain embodiments, solutions (supra) are prepared fresh prior to use. In certain embodiments, sinapinic acid (commercially available from Bruker or Sigma) is dissolved in fixation solution (e.g., about 95% ethanol:about 5% acetic acid combination) by first vortexing for one minute, followed by sonication for 30 minutes. In certain embodiments, the solution is then centrifuged for two minutes at maximum speed in a microcentrifuge. In certain embodiments, the solution is then cooled to −20° C. and protected from light.

Matrix Solution Fixation—In certain embodiments, tissue edges are delineated with an ImmPenn. In certain embodiments, fixations described herein are performed for 10 minutes at −20° C. In certain embodiments, the tissue slice is covered with the prepared cold matrix/fixative solution (10-20 µL) and incubated for 10 minutes at −20° C. Said samples are then optionally air-dried at ambient temperature. The tissue is rinsed with 10-20 µL of about 0.1% aqueous trifluoroacetic acid solution for a few seconds, then carefully removed with a pipette, and washed for a further one minute with 10-20 µL of about 0.1% aqueous TFA solution. The sample is then air-dried at ambient temperature.

The mechanical structures and/or equipment required for said analytical techniques (e.g., mass spectrometer) are well known to those skilled in the art. Many aspects of the present invention are readily amenable to automation and processing via high-throughput techniques, including, but not limited to, parallel preparation and analysis (see, for example, U.S. Pat. No. 6,900,061). In certain embodiments, aspects of the present invention relate to the use of a sprayer, nebulizer, electrospray source, or other source known to those in the art to deposit matrix material while fixing the analyte tissue sample.

Fixation and Matrix Deposition

The greatest obstacle to preparing tissues for mass spectrometry analysis by MALDI has been the conservation of tissue integrity and protein localization upon matrix deposition. This is due to the solubilization and displacement of proteins by the commonly used about 50% acetonitrile (ACN):about 50% $H_2O$ matrix solution. To overcome this limitation, cold solvent tissue fixation protocols have been combined with matrix deposition. Starting from established immunohistochemistry protocols, a series of fixative solutions have been developed that included dissolved MALDI matrices, which have been used to fix concomitantly the tissue and deposit matrix. This resulted in a histology compatible method of tissue preparation for mass spectrometry imaging. The perturbation of tissue morphology, and protein distribution were minimal, and optimized methods even maintained some subcellular structure. Matrix crystals can be removed after imaging, providing the opportunity for histology and mass spectrometry imaging of the same tissue section. This method was tested and found to be compatible with common MALDI matrices, including HCCA, sinapinic acid, and 2,5-dihydroxybenzoic acid (DHB). Frozen tissue sections were either thaw-mounted directly onto polished or ground stainless steel targets or onto glass- and indium tin oxide (ITO) coated glass coverslips. A number of different solutions commonly used for histology fixation were found to be useable for matrix solution fixation, including: (a) acetone; (b) methanol; (c) about 95% ethanol:about 5% acetic acid combination; (d) about 50% methanol: about 50% acetone combination; (e) about 10% glacial acetic acid:about 30% chloroform:about 60% absolute ethanol combination (Carnoy's Fixative); and (f) about 50% methanol:about 50% ethanol combination. Each of the aforementioned solutions was evaluated for spectroscopic quality, reproducibility, effect on tissue morphology, and image quality. In general, solvent mixtures provided better spectra than single solvent matrix solutions. Acetone combinations, for instance, gave good spectroscopic data, but dehydrated and deformed the tissue on the micrometer scale. Washing or prefixing tissue with ethanol was tested and found to be compatible with this matrix solution fixation, although the ethanol wash resulted in a decrease in overall spectroscopic intensity (sum of signal/noise {S/N} for all peaks), and the selective elimination of biomolecules.

Figure 1:
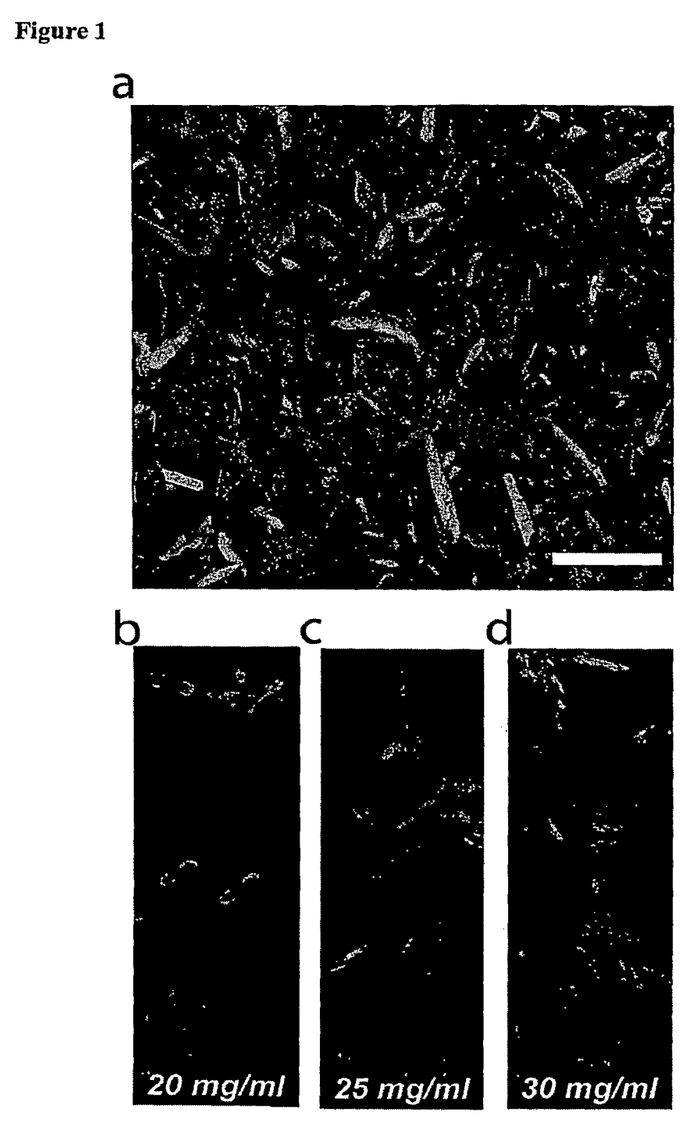
FIG. 1 depicts confocal microscopy of different concentrations of matrix crystals upon mouse brain tissue sections with a 20× dry objective, scale bar=75 cm: (a) 19.3 µm optical stack of a 25 mg/mL sinapinic acid deposition by matrix solution fixation; (b-d) single optical slices (0.4 µm) of three different matrix solution concentration depositions, 20-, 25-, and 30 mg/mL sinapinic acid respectively.
Figure 2:
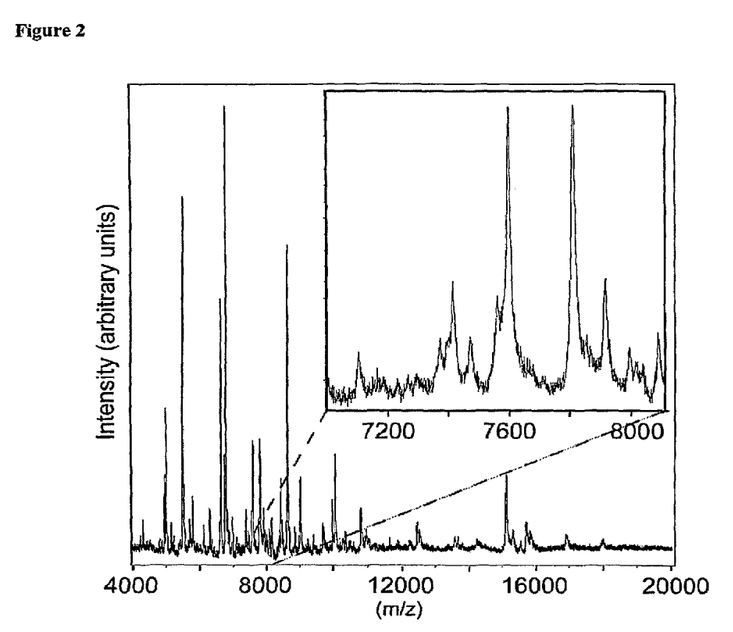
FIG. 2 depicts a representative mass spectrum taken from a normal mouse brain tissue section of 16 µm thickness from 4000 to 20000 m/z prepared by sinapinic acid solution fixation. The spectrum was produced from accumulation of 500 laser shots and is not smoothed or baseline-corrected. The inset magnifies the region of the spectrum between 7000 and 8200 m/z to represent data quality.

Next, iterative optimization was undertaken of the following parameters: type and ratio of solvents; fixation time and temperature; drying temperature; matrix concentration; ratio of matrix solution to tissue volume; and finally tissue thickness. Preparations that did not noticeably perturb tissue morphology at the microscopic (10 micron or more) level were then tested for spectroscopic quality. Spectroscopic quality was judged primarily as a function of the number of detectable peaks, and then as a function of the signal to noise of individual peaks, such that a spectrum with 10 peaks at S/N of 10 would be considered of higher quality than a spectrum with one peak at a signal to noise of 100. The following fixative solution was found to maximize both quantity and quality of analyte MS signals from tissue, while minimizing diffusion of proteins and tissue deformation—ethanol:methanol:acetonitrile:about 0.1% TFA (in water) in a 2:2:1:1 ratio, containing 25-30 mg/ml of matrix. Fresh solution (less than 12 hours old), and sonication of the matrix solutions for 30 minutes followed by a 2 minutes microcentrifugation at (15,000 g) were critical for reproducible and homogeneous crystallization (FIG. 1). Due to their delocalized π electron networks, matrix molecules have an inherent green fluorescence, allowing their monitoring by fluorescence confocal microscopy. FIG. 1 illustrates matrix crystals upon a tissue section. To maintain a constant ratio of matrix solution to tissue volume, a surrounding physical and hydrophobic barrier approximately 3 mm away from the tissue's edge was delineated using an ImmEdge Pen. With a standard fixation time of 5 minutes, followed by a room temperature drying time of approximately 5 minutes, the time required from slicing the frozen tissue to introducing it to the mass spectrometer is 10 minutes, producing high quality spectra, as illustrated in FIG. 2.

Spatial Resolution

Figure 3:
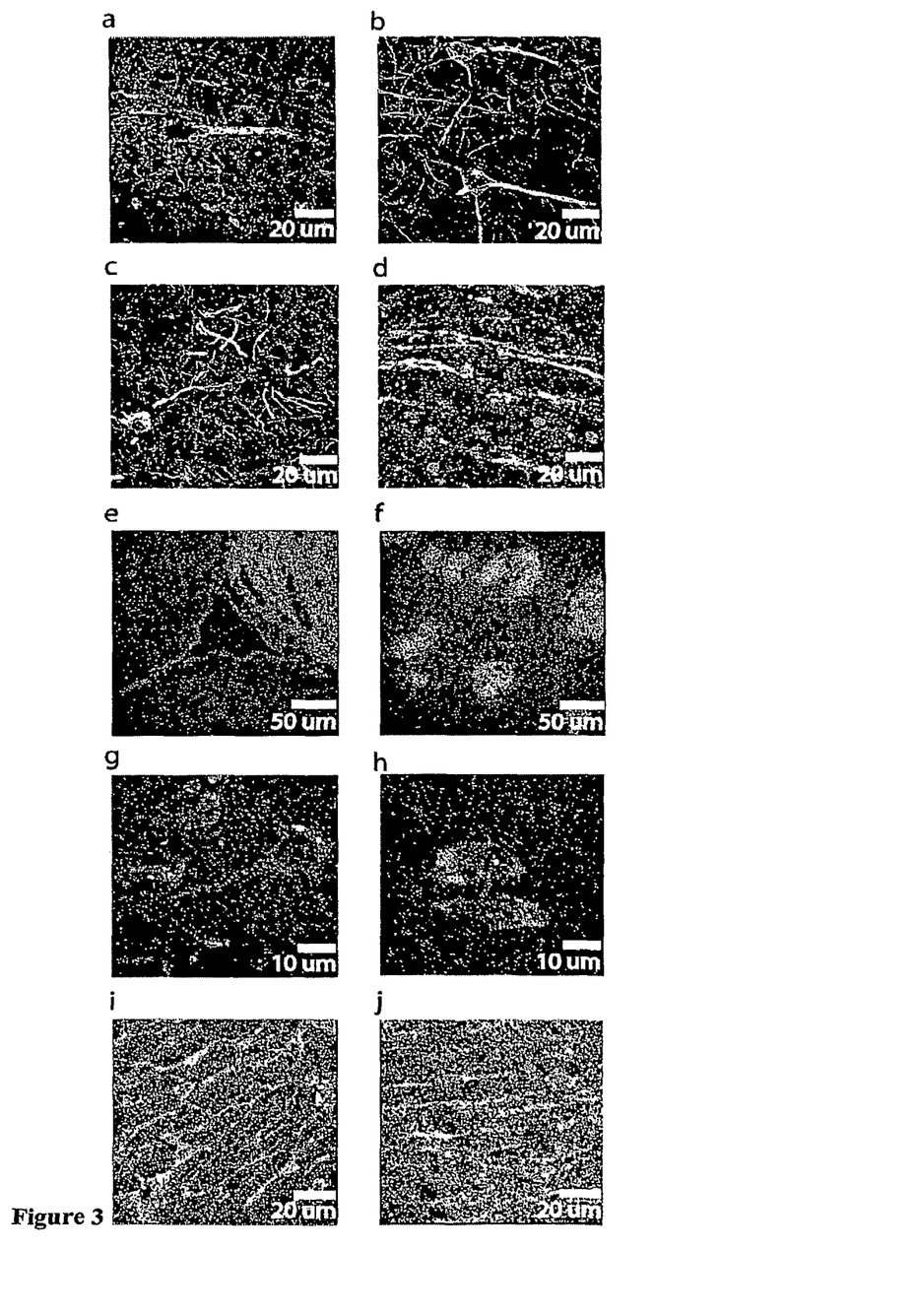

To evaluate effects of optimized methods upon spatial resolution, treated normal mouse brain specimens were subject to immunohistochemistry. FIG. 3 compares protein distribution in tissue samples that were fixed with paraformaldehyde, acetone, or with the optimized matrix solution (ethanol:methanol:acetonitrile:about 0.1% TFA in water in a 2:2:1:1 ratio). Confocal microscopy of nuclei using the fluorescent stain 4',6-diamidino-2-phenylindole (DAPI), together with antibodies against either neurofilament (FIG. 3a-d), a newly characterized soluble protein (FIG. 3e-h), or the soluble protein microtubule associated protein 2 (MAP2) (FIG. 3i-j) revealed intact grey matter-white matter interfaces and axon bundles, and intact nuclei and neurofilaments. The sample shown in FIG. 3a was fixed with paraformaldehyde as a positive control for efficient tissue fixation, and presents a characteristic neuronal pattern. In comparison, samples 3b and c were respectively fixed with the optimized solution and acetone, both efficient solvents for matrix solution fixation, and show neuronal features comparable to the paraformaldehyde control. FIG. 3*d* displays an image of a tissue section fixed with the optimized solution in the presence of the matrix sinapinic acid. After crystallization, the matrix was removed by solubilization in methanol. The neurofilament and nuclei staining indicates that matrix crystal formation as well as crystal removal has minimal effects on tissue integrity. Samples in FIGS. 3*e* and 3*f* were both fixed with acetone and stained for nuclei and a newly characterized soluble protein. Tissue integrity is observed by a clear delineation between the two hemispheres and the upper commissure in FIG. 3*e* and patterns of axon bundles in FIG. 3*f*. In FIGS. 3*g* and 3*h*, the same antibody was used to illustrate preservation of a perinuclear localization by standard fixation with paraformaldehyde (FIG. 3*g*) in comparison to fixation with our optimized solution (FIG. 3*h*). Similarly, FIGS. 3*i* and 3*j* display preservation of the MAP2 protein distribution upon treatment with either paraformaldehyde or an optimized solution of the present invention.

Figure 4:
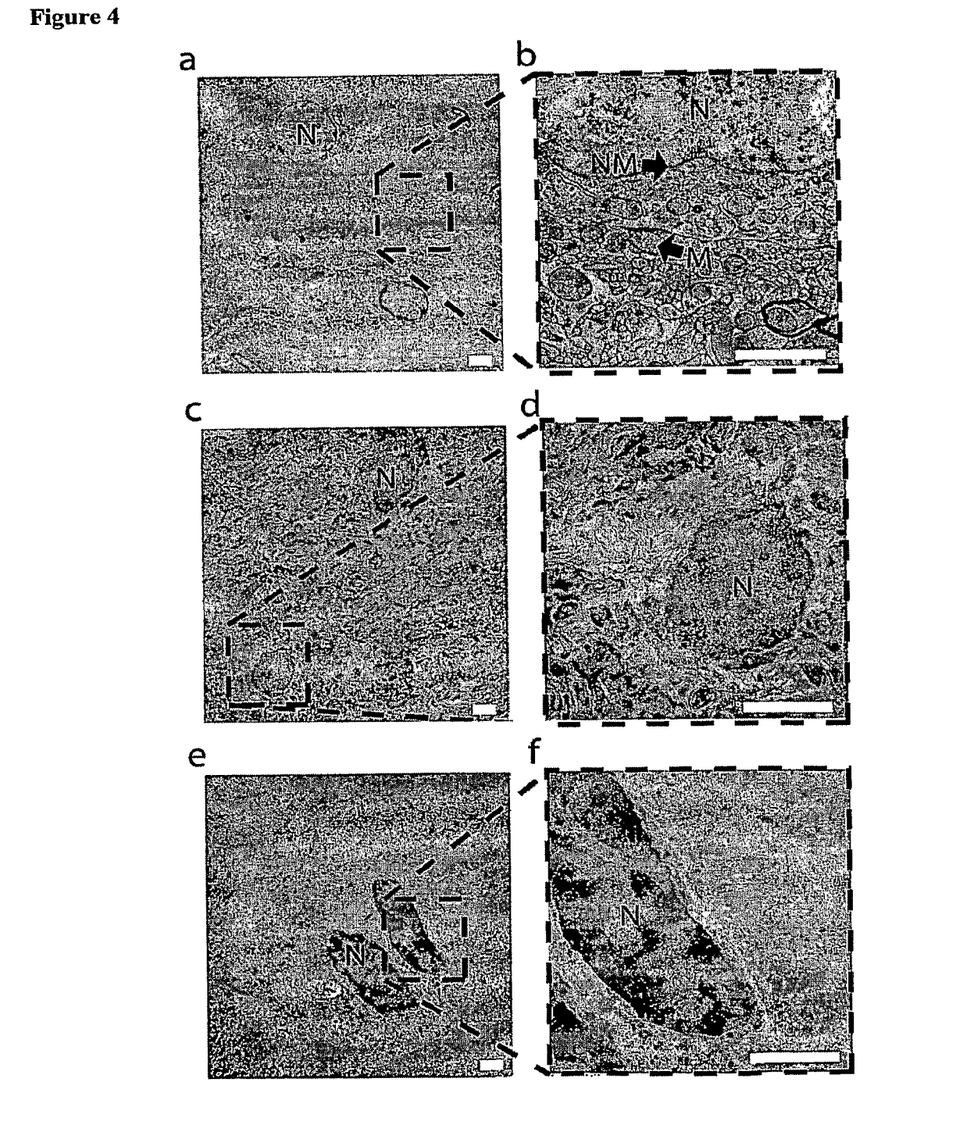
FIG. 4 depicts electron microscopy of normal mouse brain cortical tissue sections at 6800× magnification: (a,b) Control sections that have not been treated prior to standard electron microscopy preparation. Cellular ultrastructure preservation is observed; (c-f) Effect of the matrix solution fixation process upon cellular ultrastructure. Panels c and d show fixation with the cold ethanol:methanol:acetonitrile:about 0.1% TFA solution; panels e and f show fixation with cold acetone prior to standard electron microscopy preparation. The treatments appear mostly to affect cellular membranes to different degree. N indicates nuclei, M is for membrane, and NM for nuclear membrane. Scale bars=2 μm.

It was not possible to establish the matrix solution fixation imposed limits of spatial resolution using confocal microscopy, although the resolution was judged to be less than 1 µm. To better estimate limitations of spatial resolution that resulted from our treatment, electron microscopy, which exhibits at least 10 nm spatial resolution, was used. After a five minutes fixation at −20° C. of 16 µm sections of normal mouse brain tissue using the presented methanol:ethanol: acetonitrile:about 0.1% TFA solution (in the absence of matrix) or acetone, the tissue was chemically fixed, embedded, and further sectioned for electron microscopy. Subcellular structures were identified, including nuclei, cytoplasmic ribosomes, rough endoplasmic reticulum, filaments, and some nuclear double membranes (FIG. 4). However, some cellular membranes were partially disrupted, therefore minimizing delineation of subcellular compartments. Mitochondria, for example, were less well defined in treated samples, indicating that our method affects some sub-cellular structures. In regions allowing distinction, cellular membranes appeared to dilate upon solvent treatment, going from approximately 40 nm thickness to roughly 90 nm thickness.

Imaging

Figure 5:
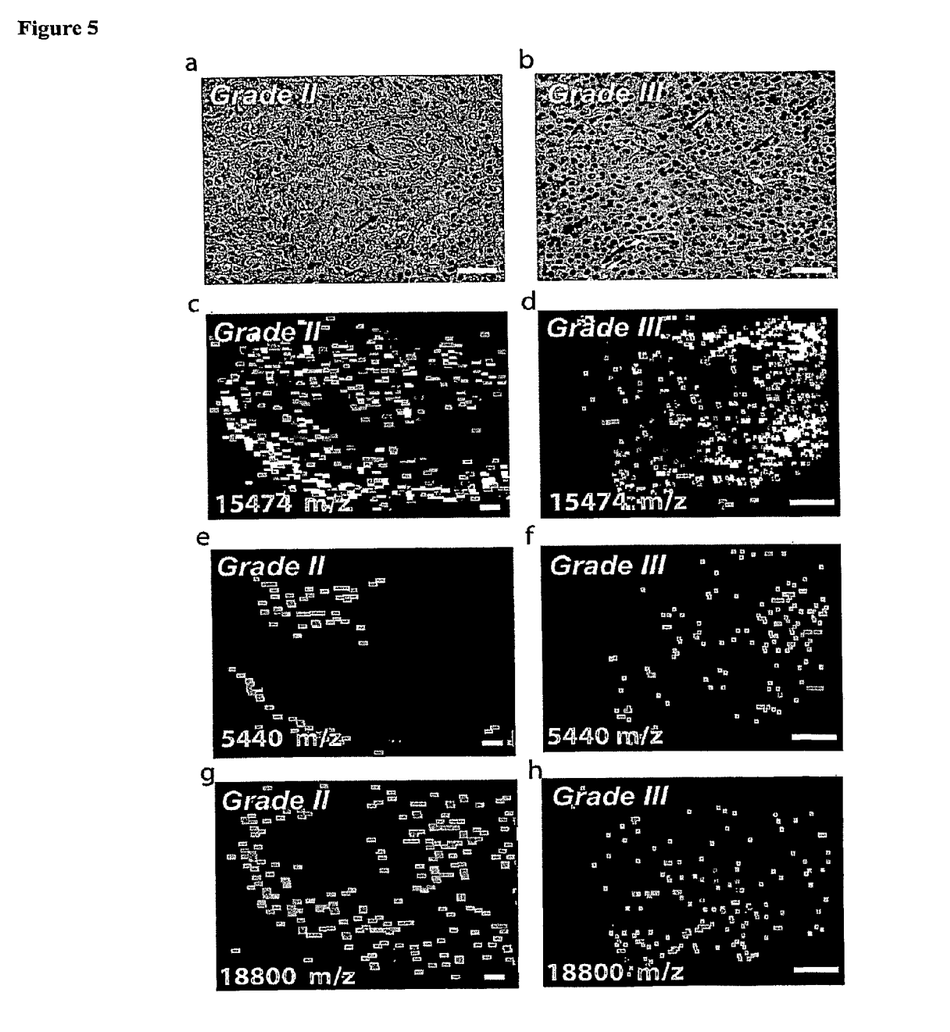

Current tissue biopsy diagnostic procedures involve microscopic imaging to assess different tissue characteristics, such as cellular composition, morphology, proliferation, tissue vascularization, and upon availability, the distribution of specific biomarkers. FIGS. 5*a* and *b* show the most common type of histological staining, a hematoxylin and eosin (H&E) staining of respectively grade II and III meningioma samples resected from a patient with malignancy recurrence and progression after initial tumor removal. Hematoxylin stains nuclei dark blue or purple while eosin stains cytoplasm pink-orange, enabling cellular resolution of some of the aforementioned histological characteristics. Some features of grade II (FIG. 5*a*) include prominent nucleoli, necrosis, and elevated mitotic rate (8 mitoses per 10 high power fields; a high power field being the area of the specimen visible under high magnification, 400× in this case), while the much higher mitotic rate (24-30 mitoses per 10 high power fields) observed in 5*b* was enough to qualify as grade III. In comparison, 5*c, e*, and *g* show selected molecular ions distribution over a grade II meningioma specimen, while *d, f*, and *h* display the corresponding molecular ions over the grade III meningioma specimen from the same patient.

The MALDI MS images of FIG. 5 represents a given ion intensity at a given location (for instance, the spatial distribution of a protein of mass 15747 is shown in FIGS. 5*c* and *d*; a different ion mass is shown in FIGS. 5*e* and *f*.) In this way, the molecular concentration as a function of location is illustrated. The observed spatial resolution of the MS images not only enables an assessment of tissue heterogeneity as observed from the H&E staining but also provides a direct assessment of a multitude of molecular features for comprehensive molecular diagnosis.

Figure 6:
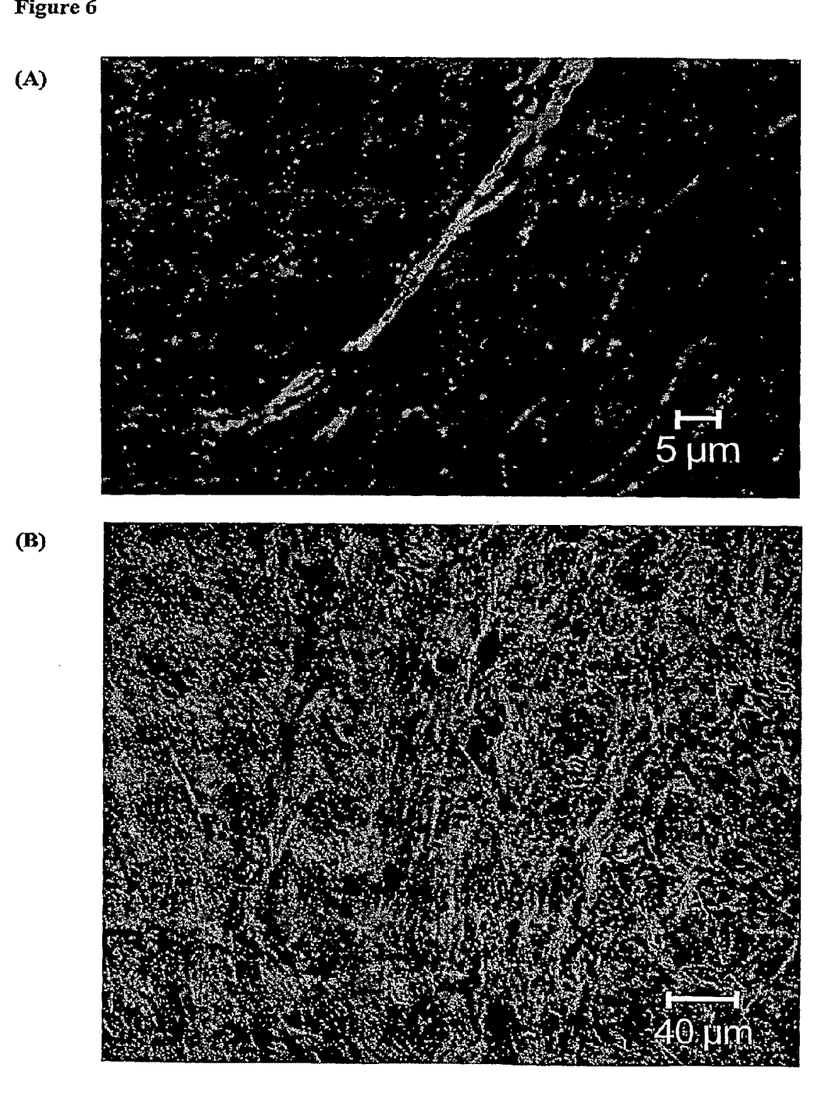
FIG. 6 depicts confocal microscopy of neurofilament-FITC neurites from single cells (bright threads) in mouse brain tissue prepared using cold acetone according to methods of the present invention: (A) 63× objective; (B) 20× objective.

FIG. 6 depicts the results from an exemplification of certain embodiments of the present invention, wherein protein distribution of neurofilament-FITC, a neuron-specific protein, has been accessed following preparation of mouse brain tissue in cold acetone according to certain embodiments the matrix solution fixation methods of the present invention detailed herein. Intact neurites of single-cells are clearly visible by confocal microscopy in FIG. 6A (bright, threadlike appearance), indicating that fixation methods of the present invention are not disruptive, effectively leaving cells whole (i.e., undamaged and/or unbroken). A broader field image (FIG. 6B) illustrates that the macroscopic properties of the tissue have also not been affected.

Figure 7:
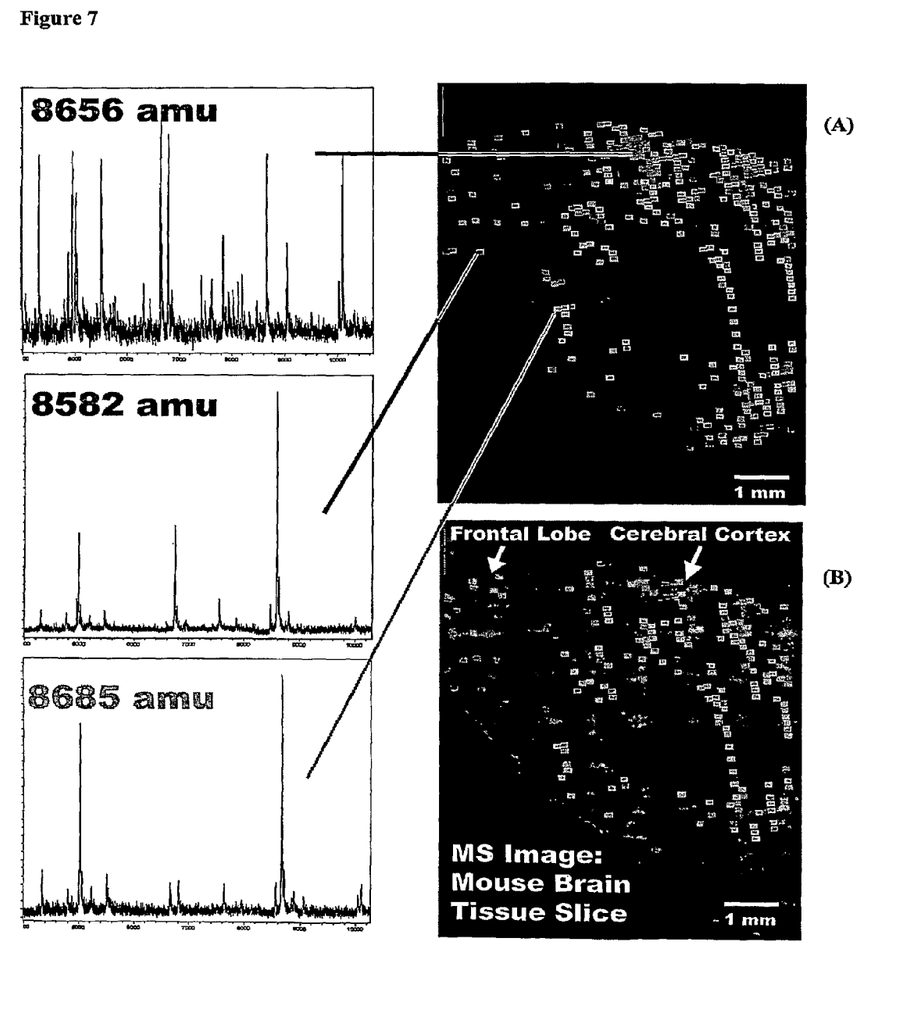
FIG. 7 depicts (A) representations of the spatial distribution of three distinct proteins of similar mass in a 100 μm resolution MALDI MS image of a saggital mouse brain tissue slice prepared using ethanol/acetic acid according to methods of the present invention; (B) MS image representation overlaid upon.

FIG. 7 illustrates that protein localization is not affected by matrix solution fixation methods of the present invention, as distinct localization is maintained for three proteins of similar mass in a 100 µm resolution MALDI MS image of a saggital mouse brain tissue slice prepared using ethanol/acetic acid according to certain embodiments the matrix solution fixation methods of the present invention detailed herein. During MALDI MS analysis, the laser is rastered 100×100 µm over the tissue slice, generating over 5000 position of analysis. Each position is then characterized by a mass spectrum of a selected mass range of interest. FIG. 7A depicts a representation of said spatial distribution, and FIG. 7B further depicts a MS image representation overlaid upon.

These experiments demonstrate the successful application of certain embodiments of the present invention, as the proteins are clearly not diffuse (i.e., they are not evenly distributed across the entire tissue). Indeed, results obtained using the novel fixation/matrix-deposition methodology of the present invention routinely outrank all published data, extending the scope of this discovery from a diagnostic method to a technique that may be practiced in all MS imaging applications and is applicable to the thousands of academic and industry practitioners of MALDI MS. The techniques provided by embodiments of the present invention improve upon the quality of the average spectra, and provide an image that does not have a perforated appearance (i.e., the image is actually an agglomerate of many tiny circles that each resulted from deposition of one droplet), as do all images that derive from spotting. Moreover, the approaches provided by embodiments of the present invention are inexpensive, very fast, and easily reproducible. For the sake of comparison, the recently patented deposition device of Caprioli (supra) takes hours to deposit sample, and costs approximately $300,000. Aspects of the present invention provide methods that require only minutes, and no additional equipment. In certain embodiments, the methods of the present invention for tissue preparation for MALDI mass spectrometry imaging make this type of analysis accessible to any established pathology or research laboratory.

The ability to image a sample and obtain the detailed spatial arrangement of compounds in an ordered target such as a slice of tissue with MALDI MSI would be of enormous value in basic biological research as well as clinical diagnosis. For example, selected ion surface maps could provide details of compound compartmentalization, site-specific metabolic processing and selective binding domains for a very wide variety of natural and synthetic compounds. To rank a new technology in the imaging category, prepared samples must be a reasonable and ideally an exact representation of the in vivo tissue. This concept was recognized over a hundred years ago and led to the development of a multitude of well-characterized histology methods for preparing tissues for microscopic study (see Clarke (1851) *Phil. Trans. Roy. Soc.* 141: 601; Carnoy (1887) *Cellule* 3:6; Blum (1893) *Vorlaufige Mittheilung. Z.w.M.* 10:314). Merging knowledge and understanding from this traditional field with mass spectrometry has led us to develop the sample preparation methods of the present invention in order to enable the routine, accurate, and comprehensive study of frozen tissue samples by MSI. Moreover, the newly developed matrix solution fixation methods provide tissue with a level of integrity that meets standard histology-pathology requirements as well as an ease of execution that makes it possible to implement in clinical settings. As the desorption and ionization processes of MALDI mass spectrometry applications involve an energy transfer from a laser source to the analyte via a crystallized compound referred to as matrix, the latter must be incorporated onto the tissue sample of interest. One of the limitations preventing the broader application of MSI has been the incompatibility of MALDI sample preparations with histology requirements. This is because solvent systems and conditions routinely used to solubilize matrix compounds can solubilize biomolecules and disturb histological and cellular structures. Methods of the present invention preserve tissue and protein structure and enable the preparation of images for publication in accordance with scientific guidelines for bioimaging applications (Editorial (2006) *Nature Methods* 3:237; Couzin (2006) *Science* 314:1866).

The matrix solution fixation (MSF) methods of the present invention are based upon histology protocols known to prevent proteins from moving or diffusing from their original location. It concomitantly denatures and precipitates analytes, while incorporating the matrix onto the tissue for further MSI analysis. Established histology fixation protocols exploit specific chemical action such as protein denaturation at low pH, protein precipitation induced by solvents, and limited protein diffusion at low temperatures (Prausnitz (2003) *Pure Appl. Chem.* 75:859).

Decreasing the fixation temperature is expected to have the positive effect of minimizing diffusion during fixation, and the potentially negative effect of promoting agglomeration (easily reversible precipitation where protein denaturation does not occur). In contrast, fixation of smaller molecules such as peptides (<1500 amu) required the use of acetone as matrix solvent, and the fixation had to be performed on dry ice to prevent diffusion. Independent of the deposition method used (spraying, spotting, and matrix solution fixation), sonication and clarification by centrifugation of the matrix solution consistently rendered significantly higher quality spectra. Such a process produces a more homogenous solution and eliminates nucleation particles that are responsible for inconsistencies in MALDI. Similarly, optimization of the matrix solution concentration also improved the deposition quality.

The methods of the present invention also afford flexibility in optimizing crystallization parameters, such as crystal size, by modulating the rate of solvent evaporation time, fixation/deposition time, and total amount of matrix applied. A variety of conditions can be exploited to favor desorption and ionization of different classes of biomolecules based on their respective physico-chemical properties, enabling the investigation of other important biomolecules such as DNA, RNA, saccharides, and lipids. Application-specific design of fixation approaches already enables a variety of molecular profiling studies (Gillespie et al. (2002) *Am. J. Pathol.* 160:449; Ahram (2003) *Proteomics* 3:413). Solvent fixation treatment of frozen tissue sections is known to solubilize lipids and cellular membrane structures, generally excluding this treatment option for electron microscopy sample preparation methods.

The sub-cellular disruption caused by our technique was ~50-300 nm, far below the 10-150 µm resolution offered on commercial MALDI mass spectrometers and on the order of the theoretical diffraction limit ($\lambda/2$) of the nitrogen laser used in this study. For direct mass spectrometry analysis of complex tissue, the quality of rendered spectra reflects a balance between resolution and the quantity of information extracted. The uniformity of tissue preparation following techniques provided by the present invention allows for direct analysis of any point of interest without subsequent data extrapolation. The MSF methods of the present invention were also extended to whole animal body perfusion, with and without matrix, and are a convenient means of preparing tissue for MSI; it will also benefit animal model studies.

Methods of the present invention compare favorably with currently used matrix deposition in discrete droplet techniques such as acoustic deposition and noncontact microdispensors (Sloane et al. (2002) *Mol Cell Proteomics* 1:490). They exhibit similar spectroscopic quality and spatial resolution as well as a faster execution, improved from the 220-300 µm range reported for acoustic reagent multispotter (ARM) process. In current practice however, the inherent resolution of said techniques cannot be realized in MS images due to a combination of mass spectrometer sensitivity and laser focus. This limits the current achievable resolution to around 10 µm, or a 20-fold improvement with highly focused lasers. This opens a world of possibilities, including imaging single cells like motor neurons; they have large cell body diameters, on the order of 40-100 µm. Moreover, it will enable higher resolution tissue imaging from ion microscope mode instruments, for which lateral resolutions ranging from 0.6-4 µm have been reported (Spengler and Hubert (2002) *J. Am. Soc. Mass Spectrom* 13:735; Luxembourg et al. (2004) *Anal. Chem.* 76:5339; Luxembourg et al. (2005) *J. Proteome Res* 4:671).

Methods of the present invention also compare favorably with an immersion method of matrix deposition that follows a tissue-washing step with organic solvents; in this method, the tissue is deprived of its lipids prior to standard matrix application (Lemaire et al. (2006) *Anal. Chem.* 78:7145). MSF preserves a higher level of tissue integrity through maintenance of the cellular ultrastructure and the general ensemble of biomolecules, including lipids. The new MSF methods of the present invention can also be extended to selectively favor distinct classes of biomolecules by taking advantage of intrinsic properties of distinct fixative solvents suitable for matrix dissolution. MSF methods combine high tissue integrity through temperature controlled diffusion kinetics with simultaneous crystallization of matrix and analytes during extraction.

Methods of the present invention also compare well with the recently developed tissue preparation of adhering tissue upon beads embedded in paraffin, and then stretching the paraffin to the tissue over a larger area (Monroe et al. (2006) *Anal. Chem.* 78:6826); both techniques are currently capable of the analysis of single, large cells. One advantage of the stretching technique is the large number of chemistries made easily available by changing the composition of the imbedded particle. Of all the techniques of MSI sample preparation, the embodiments of the present invention and the stretching technique are the only that could conceivably be used to prepare samples for both MSI and for secondary ion mass spectrometry imaging (Lechene et al. (2006) *J. Biol.* 5:20; Monroe et al. (2005) *JACS* 127:12152), which has a resolution of around 40 nm.

EXEMPLIFICATION

The invention may be understood with reference to the following examples, which are presented for illustrative purposes only and which are non-limiting.

Materials

Swiss nude male mice of 4-8 weeks of age from Charles River Laboratories (Wilmington, Mass., USA) were anesthesized and sacrificed by intra-peritonal 90 mg/kg ketamine and 10 mg/kg xylazine. All animal manipulations were carried out in the animal facility at the Brigham and Women's Hospital in accordance with federal, local, and institutional guidelines. Tumor samples were obtained from the Brain Tumor Bank in the Department of Neurosurgery, Brigham and Women's Hospital and analyzed under appropriate Institutional review board guidelines. Calibration standards and α-cyano-4-hydroxycinnamic acid (HCCA) matrix were purchase from Bruker Daltonics (Billerica, Mass., USA). Sinapinic acid was purchased from Sigma. The pan neuronal neurofilament monoclonal antibody was from Abcam (Cambridge, Mass., USA), MAP2 polyclonal antibody from Chemicon (Billerica, Mass., USA), fluorescein (FITC)-conjugated donkey anti-mouse secondary antibody was from Jackson ImmunoResearch (West Grove, Pa., USA), and Alexa 488-conjugated donkey anti-rabbit secondary antibody was from Invitrogen (Carlsbad, Calif., USA). The antibody against the newly characterized protein was raised in rabbit (Agar et al, manuscript in preparation). The nucleic acid stain DAPI was from Calbiochem (San Diego, Calif., USA). Chemicals (solvents are HPLC grade, acids and detergents) were from Fisher Scientific (Fair Lawn, N.J., USA). Glass coverslips are 22×22 mm (thickness 1: 0.13-0.17 mm) from Fisher Scientific (Pittsburgh, Pa., USA). ITO coated coverslips with busbars were 18×18 mm with resistivity from 8-12 ohms (thickness 1: 0.13-0.17 mm) from SPI Supplies (West Chester, Pa., USA). ImmEdge PEN from Vector Laboratories, Inc. (Burlingame, Calif., USA).

Sample Preparation for MALDI Mass Spectrometry Imaging

Mouse brain tissue and human tumor specimens were sectioned using a Microm HM525 cryostat from Mikron Instruments Inc. (San Marcos, Calif., USA). Method Optimization: In selecting a proper solvent combination for a given experiment, attention was also given to the surface tension effect on matrix distribution. For a specimen of dimensions 16 μm thickness with a surface of 10×5 mm, the tissue volume is 0.8 μl. The ratio recommended by the Online Information Center for Immunohistochemistry IHC World being of at least 20:1, we found that using a 20 μl volume of fixative/matrix solution was optimal. We noted that the appearance of the matrix layer is a reliable indicator of its ionization/desorption efficiency potential. The most efficient matrix layers had a homogenous and shiny appearance whereas scattered layers with a mat finish rendered lower quality spectroscopic data. In our understanding, the ability of the matrix layer to reflect light is indicative of the matrix crystals homogeneity.

Mass Spectrometry

A MALDI-TOF mass spectrometer Microflex interfaced with FlexImaging Software (inHouse version) from Bruker Daltonics (Billerica, Mass., USA) was operated in linear mode for m/z greater than 3000, and in reflectron mode for m/z less than 3000. Standard instrument parameter were used, although delayed extraction times were optimized to between 400-800 ns, depending upon the preferred mass range. To perform imaging of tissue specimens directly from coverslips in a Microflex instrument without introducing modifications of either the laser beam or molecular ions path distances, we custom made coverslip holders from original Bruker's Microflex stainless steel target with a cavity of 25×25 mm with a depth of 300 μm was produced to accommodate glass coverslips of dimensions: 22×22 mm, thickness 1 (0.13 to 0.17 mm). The coverslips are held on the target by minimal conductive adhesive tape.

Immunohistochemistry

Protocol to reduce background staining for mouse produced antibody on mouse tissue staining all performed at room temperature; tissue sections of 9 μm thickness. Blocking for 30 minutes with PBS solution: 2% normal donkey serum, 1% BSA, about 0.1% gelatin, about 0.1% Triton X-100, 0.05% Tween-20, 0.05% sodium azide. Primay for 60 minutes in P13S solution: 1% BSA, 0.01% gelatin, 0.05% sodium azide, anti-NF 1:1000, anti-MAP2 1:1000, anti-newprotein 1:1000 (Agar et al., in preparation). Rinse 3 times for 5 minutes with PBS. Secondary antibody for 45 minutes in PBS solution 2% normal donkey serum, anti-mouse fluorescein (FITC) conjugated secondary antibody 1:200 and 4,6-diamidino-2-phenylindole (DAPI) 1 μg/ml. Wash twice with PBS for 10 minutes.

Confocal Microscopy

Immunohistochemistry was visualized on a Leica TCS SP2 AOBS (Accousto Optical Beam Splitter) Spectral Confocal Microscope equipped with a 405 nm UV laser. The UV laser was used to excite DAPI at 405 nm, and the 488 nm line of the Argon laser was used to excite the FITC fluorophore. Samples were scanned at 0.275-0.623 micrometer optical slices (in the z direction). Stack images of 10-16 slices were combined using the 2D maximum projection of a series along fixed axis option. Intensity and contrast of each acquisition channel were readjusted for each sample using the "glow over under" option of the Leica Confocal Software.

Electron Microscopy

Samples were fixed in a mixture of 2.5% Glutaraldehyde and 2% Paraformaldehyde in 0.1 M sodium cacodylate buffer (pH 7.4), washed in 0.1M cacodylate buffer and postfixed with a mixture of 1% Osmiumtetroxide+1.5%

Potassium ferrocyanide for 30 minutes (control was 2 hours), washed in water and stained in 1% aqueous uranyl acetate for 30 minutes (control was 1 hour) followed by dehydration in grades of alcohol (about 50%, 70%, about 95%, 2×100%) and then infiltrated and embedded in TAAB Epon. (Marivac Canada Inc. St. Laurent, Canada)

Ultrathin sections (about 60-80 nm) were cut on a Reichert Ultracut-S microtome, picked up on to coppergrids, stained with 0.2% lead citrate and examined in a "Tecnai $G^2$ Spirit BioTWIN" Transmission electron microscope. Images were taken with a 2k AMT CCD camera.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of generating an image of a sample, wherein the image details the spatial distribution and abundance of compounds in the sample, comprising:
   (a) combining:
      a fixative selected from the group consisting of: (i) acetone; (ii) methanol; (iii) about 95% ethanol and about 5% acetic acid; and (iv) 1 part methanol:1 part ethanol:0.5 parts acetonitrile:0.5 parts aqueous solution of about 0.1% TFA; with
      a mass spectrometry matrix material selected from the group consisting of: sinapinic acid and α-cyano-4-hydroxycinnamic acid,
      to give a fixative solution;
   (b) treating the sample selected from the group consisting of: a tissue sample, a cell culture, a single cell, a cellular extract, and a plurality of cells immobilized on a substrate surface, with said fixative solution, at a treating temperature from −78° C. to 37° C. and for a period of time sufficient to inhibit compounds in the sample from moving or diffusing from their original location therein, thereby forming a fixed sample; and
   (c) imaging the fixed sample using MALDI mass spectrometry, thereby generating the image of the sample.

2. The method of claim 1, further comprising drying said fixed sample.

3. The method of claim 1, wherein the period of time is about 10 minutes.

4. The method of claim 1, wherein the temperature is about −20° C.

5. The method of claim 1, further comprising rinsing said fixed sample, and drying said rinsed fixed sample, and optionally rinsing said rinsed and dried fixed sample a second time, and drying said optionally rinsed fixed sample, wherein each rinsing comprises rinsing with a 0.1% solution of trifluoroacetic acid.

6. The method of claim 1, further comprising freezing said sample.

7. The method of claim 1, wherein said fixative is about 95% ethanol and about 5% acetic acid.

8. The method of claim 1, further comprising thaw-mounting said sample.

9. The method of claim 1, wherein treating the sample with the solution comprises covering the sample with a volume of the fixative solution.

10. The method of claim 9, wherein the volume of the fixative solution is 10-20 μL.

11. The method of claim 1, wherein the concentration of the mass spectrometry matrix material in the fixative solution is about 20-30 mg/mL.

* * * * *